United States Patent [19]

Holden

[11] Patent Number: Plant 7,322

[45] Date of Patent: Sep. 11, 1990

[54] VARIETY OF GERANIUM NAMED JUDY

[75] Inventor: Douglas Holden, Solvang, Calif.

[73] Assignee: Bodger Seeds, Ltd., El Monte, Calif.

[21] Appl. No.: 346,136

[22] Filed: Apr. 28, 1989

[51] Int. Cl.[5] ..... A01H 5/00

[52] U.S. Cl. ..... Plt./68

[58] Field of Search ..... Plt./68

*Primary Examiner*—James R. Feyrer

*Attorney, Agent, or Firm*—Webb, Burden, Ziesenheim & Webb

[57] ABSTRACT

A new Geranium cultivar is distinguished by its floriferousness, light salmon color, compactness, lateral and procumbent growth habit, heat tolerance, better cutting producer, full growth and dark zoning presence.

1 Drawing Sheet

BACKGROUND OF THE NEW PLANT

The present invention comprises a new and distinct cultivar of Pelargonium known by the varietal name Judy (Oglevee No. 1312, Bodger No. 6GM 129-6). The new variety was discoered in a selective breeding program to develop hybrid varieties for vegetative propagation by Mr. Douglas Holden. The new variety is a selection from the crossing of the seed parent, Salmon Floral Cascade with the pollen parent Pinto Red.

Salmon Floral Cascade is a commercially available vegetatively propagated cutting variety from Australia and which includes strains of *Pelargonium frutetorum* and *Pelargonium peltatum*. Pinto Red is a commercially available salmon single flower zonal (*Pelargonium* × *hortorum*) $F_1$ hybrid seed geranium.

The new cultivar was discovered in August of 1986 at Bodger Seeds, Ltd. in El Monte, Calif., was first asexually reproduced by cuttings by Bodger Seeds, Ltd. at El Monte, Calif. and has been repeatedly asexually reproduced by cuttings at Oglevee Ltd. in Connellsville, Pa.

The hybrid is a different color (coral) and has larger flowers than the closest comparative variety, Salmon Floral Cascade.

The new cultivar, when grown in a glass greenhouse in Connellsville, Pa., using full light, 60° F. temperture, 68° day temperature, 71° F. vent temperature, and grown in a soilless media of constant fertilizer of 200–250 parts per million nitrogen and potassium, has a response time from a rooted cutting to a flowering plant in a four inch (10 cm) pot of six weeks.

DESCRIPTION OF THE DRAWING

The accompanying drawing illustrates a new cultivar, the color being as true as possible with color illustrations of this type.

DESCRIPTION OF THE NEW PLANT

The following detailed descriptions set forth the characteristics of the new cultivar. The data which define these characteristics were collected from asexual reproductions carried out by Oglevee Ltd. in Connellsville, Pa. The plant histories were taken on plants blossomed under full light in a greenhouse and which were potted as a rooted cutting on Aug. 1, 1988 and flowered on Sept. 15, 1988. Color readings were taken indoors under 200–220 foot candles of cool white fluorecent light. Color references are primarily to the R.H.S. Colour Chart of The Royal Horticultural Society of London.

THE PLANT

Classification:

*Botanical.*—Hybrid Species. Semi-dwarf; compact; free basal branching; lateral and procumbent growth habit, nice mound form.

Height: 16–17 cm the media surface. Free and early flowering, free branching without having to pinch, very floriferous flowering, very definite dark zone.

Strength: Lateral branching that forms a mound shape without any support.

Foliage: Zoning present, stalked leaf attachment.

Leaves:

*Size.*—5.5–8.5 cm across.

*Shape.*—Reniform, cordate base.

*Margin.*—Crenate.

*Texture.*—Pubescent; dull (not reflective).

*Color.*—Top: Outer margin and left center: Green group 137A; Zone — Greyed-purple group 187A; Bottom — Yellow-green group 147B.

*Ribs and veins.*—Palmate venation; Yellow-green group 147C.

Petioles: 4–8.5 cm in length; Yellow-Green group 146C.

Stem:

*Color.*—Yellow-green group 146C.

*Internodes.*—1–3 cm in length.

THE BUD

Shape: Upright; hemispherical cluster.

Size: 1–1.5 cm across.

INFLORESCENCE

Blooming habit: Continuous; upright many smaller blooms, self-cleaning.

Size: 5–7 cm across.

Borne: 4–7 cm above foliage; florets on pedicel; pedicel on peduncle.

Florets:

*Form.*—Flat to slightly cupped.

*Color.*—Red group 41C.

*Petals.*—12–15 in number; separate not united; margin entire obovate; smooth; flat to slightly cupped.

*Floret size.*—2.5–3.5 cm across.

*Texture and appearance.*—Smooth.

Petaloids:

*Quantity.*—3–8.

*Shape.*—Narrow, elongated, twisted; some tubular.
*Color.*—Red group 41C.

Pedicel:
*Size.*—2–2.5 cm in length.
*Color.*—Greyed-purple group 183C to Yellow-green group 146C at a point where pedicle attaches to peduncle.

Peduncle:
*Size.*—Arises from the node, opposite the leaf petiole; 13–15 cm in length.
*Color.*—Yellow-green group 146C with a cast of greyed-purple group 183B at umbel end.

Lasting quality: This variety is very heat tolerant both indoors and in the outdoor garden and is a continuous bloomer.

REPRODUCTIVE ORGANS

Stamens:
*Anters.*—2 mm in length.
*Filaments.*—5–6 mm in length; white in color.
*Pollen.*—Golden brown.

Pistils:
*Number.*—1 with 5 or 6 parted stigma.
*Length.*—7–8 mm.
*Stigma.*—One, 5 or 6 parted at maturity, red-purple color.

*Style.*—2–3 cm in length; pink to red-purple in color according to age.

Ovaries: 4–5 mm in length; superior; very pubescent, pale green.

Fruit: Occasional fruit note, pale green in color.

This unique variety adds a new dimension to the geranium family. The plant exhibits a neat mound habit that may be used in either hanging baskets or the traditional ground bed. The dark zone compliments the medium green foliage creating an eye catching novelty in the garden. Many small flower clusters create a large continuous bouquet of light salmon color. In comparing this new variety with the current IVY varieties now on the market, one would find it more floriferous; a much fuller growth habit; better heat tolerance; and a much better cutting producer.

I claim:

1. A new and distinct variety of geranium plant substantially as herein shown and described and characterized by its floriferousness, light salmon color, compact habit, lateral and procumbent growth habit, heat tolerance, better cutting producer when compared to other ivy Geranium varieties, full growth and dark zoning.

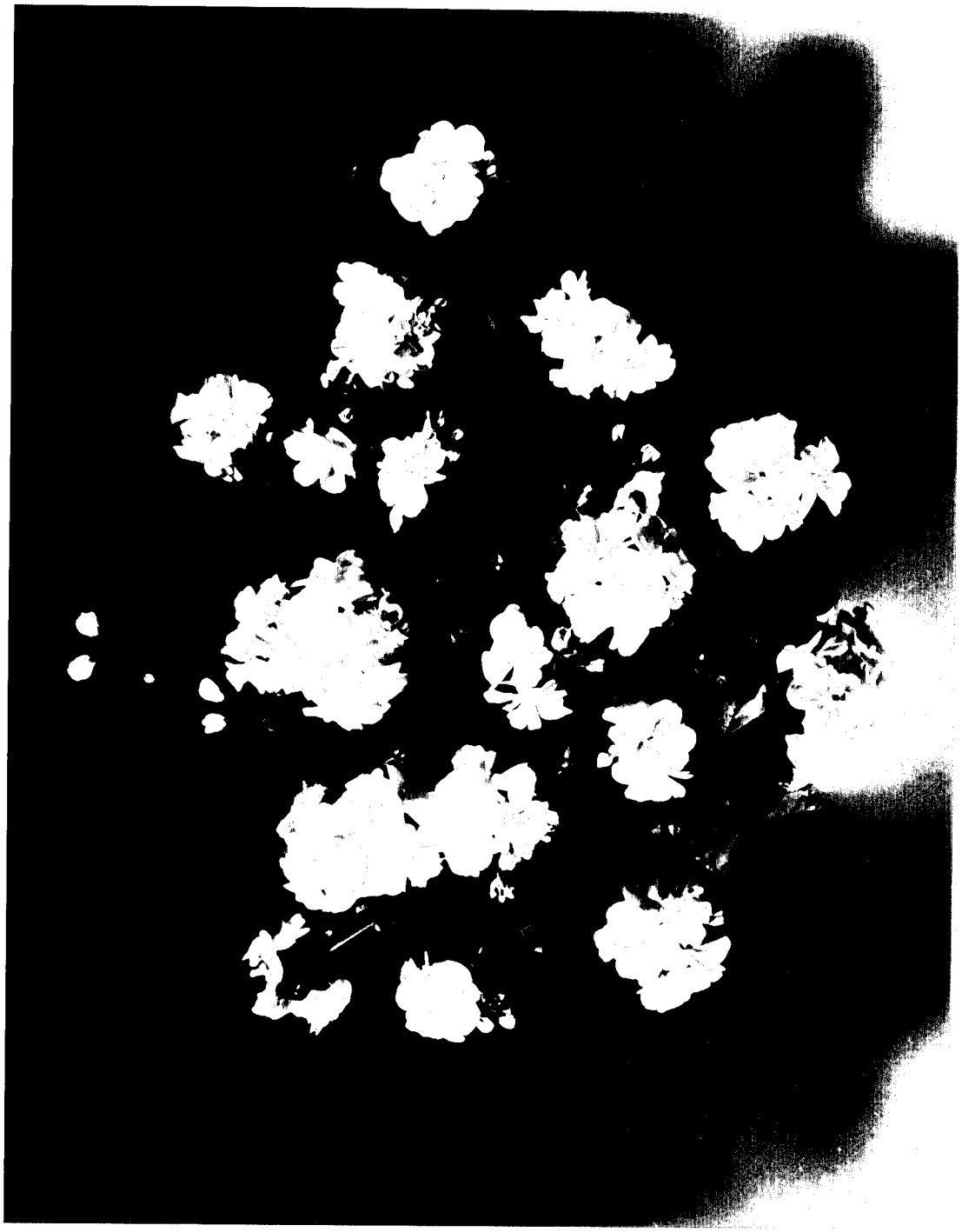

* * * * *